United States Patent [19]

Brown et al.

[11] Patent Number: 4,737,307

[45] Date of Patent: Apr. 12, 1988

[54] SKIN CLEANSER CAPABLE OF REMOVING SMEGMA AND SURFACE BACTERIA, FUNGUS AND VIRUSES FROM SURFACE OF SKIN

[76] Inventors: Robert L. Brown, 3917 Evergreen, Irving, Tex. 75061; Elizabeth C. Stewart, No. 6 Pinecreek La., Houston, Tex. 77055

[21] Appl. No.: 76,781

[22] Filed: Jul. 23, 1987

Related U.S. Application Data

[63] Continuation-in-part of Ser. No. 908,697, Sep. 18, 1986, Pat. No. 4,692,262.

[51] Int. Cl.$^4$ ................................................ C11D 3/48
[52] U.S. Cl. ...................................... 252/106; 252/173; 252/174.21; 252/DIG. 5; 424/149; 514/358
[58] Field of Search ........... 252/106, 107, 173, 174.21, 252/542, 550, 559, DIG. 5, DIG. 14; 424/149; 514/358

[56] References Cited

U.S. PATENT DOCUMENTS

| | | | |
|---|---|---|---|
| 3,147,124 | 9/1964 | Wentworth | 424/149 |
| 3,787,566 | 1/1974 | Gauvreau | 514/358 |
| 4,035,483 | 7/1977 | Bunyan | 424/149 |
| 4,296,103 | 10/1981 | Laso | 424/149 |

FOREIGN PATENT DOCUMENTS

| | | |
|---|---|---|
| 15255 | 11/1985 | European Pat. Off. . |
| 59024 | 5/1978 | Japan . |
| 78909 | 5/1985 | Japan . |
| 188316 | 9/1985 | Japan . |

Primary Examiner—Paul Lieberman
Assistant Examiner—Hoa Van Le
Attorney, Agent, or Firm—Pravel, Gambrell, Hewitt, Kimball & Krieger

[57] ABSTRACT

A cleansing composition capable of removing smegma comprises in an aqueous solution a cleansing agent comprising a mixture of surface active agents in the indicated amounts as follows:

(i) from a trace to 0.2% by weight, based on the total weight of said composition, as an active material of cetylpyridinium chloride,
(ii) from a trace to not more than 20 ppm chlorine dioxide, plus 20 ppm sodium hypochlorite,
(iii) from a trace to 1% by weight, based on the total weight of said composition as an active material, of polyoxyethylene (20) sorbitan monostearate, and
(iv) sodium benzoate from a trace to 2%.

5 Claims, No Drawings

SKIN CLEANSER CAPABLE OF REMOVING SMEGMA AND SURFACE BACTERIA, FUNGUS AND VIRUSES FROM SURFACE OF SKIN

This application is a continuation-in-part of application Ser. No. 908,697, filed Sept. 18, 1986, now allowed as a U.S. Pat. No. 4,692,262.

BACKGROUND OF THE INVENTION

1. Field of the invention the present invention relates to a cleansing composition suitable for use as a topical cleanser for removing smegma, candida and other fungus, bacteria and viruses from the surface of the skin of humans and animals.

2. Description of the prior art there have been proposed several cleaning agents for cleaning and or removing oily secretions from human skin, particularly the facial area, such as U.S. Pat. No. 3,988,255 and U.S. Pat. No. 4,495,079 as well as U.S. Pat. No. 4,287,101 which discloses a detergent composition for removing sebum or smegma from soil spots in fabrics. None of these, however, are considered suitable for topical application to human skin and particularly where traces of such material may be ingested. Also, there are various quaternary ammonium compounds which act as emulsifiers of lipo-protiens and which also remove or destroy fungus, bacteria and some viruses from the surface of the skin.

SUMMARY OF THE INVENTION

The present invention relates to a new and improved cleaning composition which serves as a topical cleanser for removing accumulations of smegma from the surface of the skin and particularly from the skin in the genital area. This invention is useful in removing smegma both from human and animal's organs, particularly horses, which suffer from so-called beans of smegma which collect on a horse's penis. Because of the waxy or cheese-like nature of smegma, which is secreted from sebaceous glands, ordinary bath soap is not always effective in the complete removal of this material. Also, because of the fatty constituents formed in smegma, it is a host for the growth of a mycobacteria. This invention will also act as a deodorizer.

The present invention contains a variety of germicidal agent inhibitors with different mechanisms and is candicidal, fungicidal bacteriocidal and somewhat viricidal and thus effective for removing surface bacteria, fungus and viruses.

An object of the present invention is to provide a skin cleanser which combines cleansing agents which are hypoallergenic and non-irritating to the skin, particularly in sensitive areas such as about the genitals, both male and female, and which is also suitable for human ingestion and is germicidal, tuberculocidal, fungicidal and virocidal. Yet another object is to provide a skin cleanser capable of removing smegma from the genital area without irritating the skin which in that area is particularly sensitive.

The present invention provides a skin cleanser for topical application which is capable of softening and removing smegma from the skin and removing bacterial, fungus, yeast or candida and cleansing superficial wounds or surface infections without causing irritation to the treated area or to body cavities. The preferred cleanser is a mixture of water with the following amounts of cleansing agents:

(i) from a trace to 0.2% by weight, based on the total weight of said composition, as an active material of cetylpyridinium chloride,
(ii) from a trace to not more than 50 ppm chlorine dioxide, plus 20 ppm sodium hypchlorite,
(iii) from a trace to 1% by weight, based on the total weight of said composition as an active material, of polyoxyethylene sobritan monostearate (tween-60). Also, artificial coloring or flavors or natural, non-sugar sweetener may be added if desired, and
(iv) sodium benzoate from a trace to 2%.

DESCRIPTION OF THE PREFERRED EMBODIMENT

The genital skin cleanser formulation of this invention may be in the form of a lotion, spray, cream, gel, or foam, as desired. The cleansing function of the composition is provided principally by the active ingredients of cetylpyridinium chloride and polysorbate 60 (tween 60) which is a polyoxyethylene sorbitan monosterate.

It is also possible to include small amounts of other additives such as fragrances, flavors, sweeteners, coloring agents or foaming agents or the like.

This cleanser is to be applied topically to the genital area to clean such areas including the removal of accumulated smegma and the microbiological organisms which may be accumulated therewith. Smegma provides a culture medium or host material for such microbiological organisms. It will be appreciated that the cleanser composition of the present invention is hypoallergenic and non-irritating both to the human skin and to the tissue forming body cavities (mucosal lining tissue).

This cleanser provided by this composition is useful both on humans and animals and is candicidal, bacteriacidal, and viricidal when put in contact with surface bacterial mycotic and yeast infections as well as surface viruses. This cleanser is useful in treating candida as well as removing smegma, a collection of bacteria, skin cells or sebacious secretious both in men and horses.

We claim:

1. A skin cleanser capable of softening and removing smegma and microbiological organisms which may be associated therewith from human or animal skin which comprises a mixture containing:

from a trace to 0.2% by weight, based on the total weight on said composition, as an active material of cetylpyridinium chloride, from a trace to not more than 20 ppm chlorine dioxide, plus 20 ppm sodium hypochlorite, from a trace to 2% by weight, based on the total weight of said composition as an active material, of polyoxyethylene (20) sorbitan monostearate; and from a trace to not more than 2% sodium benzoate.

2. The invention of claim 1 wherein the mixture is suitable for oral ingestion.

3. The invention of claim 1 wherein the mixture is non-irritating to the skin in the genital area or the body cavities.

4. A topical skin deodorizer reducing or eliminating the odor from human or animal skin caused by accumulation of smegma and microbiological organisms which may be associated therewith which deodorizer comprises a mixture containing:

from a trace to 0.2% by weight, based on the total weight of said composition, as an active material of cetylpyridinium chloride, from a trace to not more than 20 ppm chlorine dioxide, plus 20 ppm sodium hypochlorite,
from a trace to 2% by weight, based on the total weight of said composition as an active material, of polyoxyethylene (20) sorbitan monostearate; and
from a trace to not more than 2% sodium benzoate.

5. A topical cleanser for removing bacteria, fungus and viruses from the surface of the skin of both human and animals comprising a mixture which contains:

from a trace to 0.2% by weight, based on the total weight of said composition, as an active material of cetylpyridinium chloride,
from a trace to not more than 20 ppm chloride dioxide, plus 20 ppm sodium hypochlorite,
from a trace to 0.2% by weight, based on the total weight of said composition as an active material, of polyoxyethylene (20) sorbitan monostearate; and
from a trace to not more than 2% sodium benzoate.

* * * * *